United States Patent [19]

Boozalis et al.

[11] 4,048,241
[45] Sept. 13, 1977

[54] PROCESS FOR PREPARING 1,1,1-TRICHLOROETHANE

[75] Inventors: Theodore S. Boozalis; Darryl E. Cragar; John B. Ivy; Gordon G. Willis, all of Lake Jackson, Tex.

[73] Assignee: The Dow Chemical Company, Midland, Mich.

[21] Appl. No.: 563,940

[22] Filed: Mar. 31, 1965

Related U.S. Application Data

[63] Continuation-in-part of Ser. No. 462,701, April 22, 1974, abandoned.

[51] Int. Cl.$^2$ ............................................. C07C 19/00
[52] U.S. Cl. ........................... 260/658 R; 260/654 D; 260/654 H; 260/656 R; 260/657 P; 260/654 S
[58] Field of Search ............... 260/663, 658 R, 654 D, 260/654 H, 654 S, 652 P

[56] References Cited
U.S. PATENT DOCUMENTS

| 3,345,421 | 10/1967 | Brown | 260/653 |
|---|---|---|---|
| 3,637,875 | 1/1972 | Correia et al. | 260/654 H |
| 3,776,969 | 12/1974 | Lobunez | 260/658 R |

Primary Examiner—Delbert E. Gantz
Assistant Examiner—Joseph A. Boska
Attorney, Agent, or Firm—Glwynn R. Baker

[57] ABSTRACT

A process for preparing 1,1,1-trichloroethane from ethylene and chlorine by hydrochlorinating the ethylene in the presence of aluminum chloride in a liquid phase reaction zone followed by chlorination of the resulting reaction product and finally by hydrochlorination of the effluent from the chlorinator in the presence of ferric chloride. The principal product of this reaction is 1,1,1-trichloroethane. Numerous by-products and partially chlorinated and unsaturated chlorohydrocarbons are also produced but, in the major part, these are recyclable and produce, upon being recycled to the appropriate step, the precursors of or the desired 1,1,1-trichloroethane product.

4 Claims, 1 Drawing Figure

PROCESS FOR PREPARING 1,1,1-TRICHLOROETHANE

CROSS-REFERENCE TO RELATED APPLICATION

The present Application is a continuation-in-part of our previous Application Ser. No. 462,701 filed Apr. 22, 1974, now abandoned.

BACKGROUND OF THE INVENTION

The hydrochlorination of ethylene in the presence of a Friedel-Crafts metal halide catalyst is an old and well-known procedure. The art employs principally ethylene and a substantially high purity hydrogen chloride in a boiling bed reactor. The composition of the boiling bed is substantially the product of the hydrochlorination. Many of the Friedel-Crafts metal halide catalysts have been suggested and depending upon the conversion, temperature of reaction, pressure, etc., the entire scope is employed. Aluminum chloride or ferric chloride, however, are the preferred and most commonly referred-to metal halide Friedel-Crafts catalysts. The principal product of this reaction with ethylene is ethyl chloride. It has become common practice to purify the ethyl chloride from this reaction prior to its use in preparing any number of more highly chlorinated materials. Likewise, the thermochlorination of ethyl chloride is a well-known process. The temperature, pressure, and the ratio of chlorine, with or without catalysts, dictate the product which is obtained. Many processes are known which integrate a di- and trichloro- product such as, for example, chlorinating ethyl chloride to 1,1-dichloroethane recycling the 1,1-dichloroethane with the ethyl chloride feed and producing therefrom 1,1,1-trichloroethane. Several techniques have been disclosed for carrying out such a process. Again in each of these processes, it is normal that the effluent product of the chlorination is separated into the desired product and recycle streams. Some desired product may be recycled as a temperature control, thus a chlorination control medium. The hydrochlorination of unsaturated partially chlorinated hydrocarbons such as vinyl chloride, vinylidene chloride, cis- and trans-dichloroethylene, are each documented in the prior art. The use of ferric chloride and/or aluminum chloride as the metal halide Friedel-Crafts catalyst for these hydrochlorinations is also well known. The separation of each of the products of the hydrochlorination of one or more of the unsaturated partially chlorinated hydrocarbons is a rather lengthy procedure requiring several distillations to obtain high purity products. It is evident from the prior art that the skilled technician approaches the preparation of polychlorinated ethylenes and ethanes in a stepwise manner preferring to separate the intermediate products and purify them before employing them in the next step. This procedure necessitates several large pieces of purification equipment intermediate to the various steps and oftentimes results in compounds being present as impurities in the desired product which create problems in the next step unless removed by chemical means.

It would therefore be advantageous if there were provided a process whereby ethylene and chlorine were the two external reactants introduced into a process and therefrom produce 1,1,1-trichloroethane with a minimum of intermediate separations of reaction products in order to provide feeds for each of the steps of a multi-step process.

It is therefore an object of the present invention to provide such a process.

BRIEF DESCRIPTION OF THE INVENTION

In accordance with the present invention, with particular attention to the drawing, FIG. 1, ethylene 1 is mixed with hydrogen chloride (15) and fed to a hydrochlorinator A wherein the ethylene is hydrochlorinated to ethyl chloride 3. The reaction is conducted in a boiling bed of ethyl chloride containing aluminum chloride catalyst dispersed throughout. The resulting gaseous product (ethyl chloride) stream 3 of this first hydrochlorination is then admixed with a recycle fraction 20 and chlorine and thermally chlorinated in thermal chlorinator B. The recycle fraction 20, obtained from the separation of products in latter steps, has a boiling point between about 37° C and about 60° C and is principally 1,1-dichloroethane. The thermal chlorination is carried out at between about 400° and 550° C. The resulting product stream 5 of this thermal chlorination is subjected to a liquid quench C wherein those chlorinated hydrocarbons boiling above about 40° C are converted from the gaseous state to the liquid state. The nonliquefied gases 6 of the product effluent stream under the quench condition, primarily hydrogen chloride, vinyl chloride and vinylidene chloride, and any unreacted ethylene and taken overhead. The liquid 7 resulting from the quench C of the product effluent from the thermal chlorinator B is in part used as the quench liquid and in the greater part is admixed with the vinyl chloride, vinylidene chloride and hydrogen chloride and any unreacted ethylene overhead fraction from the quench C and the resulting mixture 10 introduced into a liquid hydrochlorinator D in which ferric chloride is the metal halide Friedel-Crafts catalyst. Thus, effectively, the entire effluent from the thermal chlorinator is quenched and passed directly to the ferric chloride hydrochlorination reactor D. This procedure eliminates a distillation between steps in the process; however, it increases the severity of the final product purification step wherein the 1,2 dichloroethane, produced in the reactions and which will now appear as an impurity with the 1,1,1-trichloroethane product, is removed. The purification may consist of a distillation of the product stream 11 from the hydrochlorinator D. As illustrated the first distillation E separates the lights 14 predominantly hydrogen chloride, and minor proportions of ethylene, vinyl chloride, ethyl chloride and vinylidene chloride. The liquid distilland (bottoms) from this distillation E are further distilled at F to separate the 1,1-dichloro ethane and the near boiling components cis- and trans-dichloroethylenes, stream 17. The bottoms from this still F are further distilled G to obtain 1,1,1-trichloroethane 18 and a bottoms of higher boiling components 19 ethylene dichloride, trichloroethylene, 1,1,2-trichloroethane and unsymmetrical tetrachloroethane.

The cis- and trans-dichloroethylenes, produced in small amounts in the thermal chlorinator, have boiling points such that the cis isomer is practically impossible to separate from the recycle 1,1-dichloroethane by distillation. If both isomers or the cis isomer alone are allowed to remain with the recycle 1,1-dichloroethane, they pass through the thermal chlorinator and hydrochlorinator essentially unaffected, thereby continuously increasing in concentration in the recycle, 1,1-dichloroethane.

The efficiency of the thermo chlorinator and the ferric chloride hydrochlorinator are improved if the cis- and trans-dichloroethylenes are maintained at a relatively low level by removal from the recycle 1,1-dichloroethane stream 20 prior to its use in the thermal chlorinator. Two procedures are provided for this removal: one consists of separating out the trans by distillation and allowing the cis to come to equilibrium with trans at the thermal chlorinator reaction temperature while in the thermal chlorinator. The other is to cold chlorinate the recycle stream during its return to the thermal chlorinator and convert the cis- and trans-dichloroethylenes into high boiling compounds.

The recycled fraction 14 consists of any ethylene, which has passed through the reactions unreacted or which is produced in the thermal chlorination, along with the hydrogen chloride, which has not reacted in the hydrochlorinator, as well as the ethyl chloride, and small amounts of vinyl chloride and vinylidene chloride. These components are returned to the process, about one-half of the stream 14 represented by stream 15 provides the hydrogen chloride for the hydrochlorination of the ethylene in hydrochlorinator A. The excess hydrogen chloride 16 is withdrawn from the process.

In an alternative procedure (see dotted lines FIG. 1) in accordance with the present invention, the above principal steps are carried out with the single exception that the liquid 7 resulting from the quench of the product effluent from the thermal chlorinator B is in part used as the quench liquid and in the greater part is forwarded to a boiling bed dehydrochlorinator H containing a Friedel-Crafts catalyst, particularly iron chloride, and more particularly about 1000 ppm iron chloride. The dehydrochlorination reactor is operated at conditions which primarily dehydrochlorinate 1,1,1-trichloroethane to vinylidene chloride, thus permitting separation of 1,2-dichloroethane from the reaction stream.

The gaseous products 8 resulting from the dehydrochlorination in H, (those boiling below about 60° C.) are admixed with the vinyl chloride, vinylidene chloride and hydrogen chloride and any unreacted ethylene overhead fraction stream 6 from the quench tower C and the resulting mixture 10 introduced into a liquid hydrochlorinator D in which ferric chloride is the metal halide Friedel-Crafts catalyst. The high boiling materials 9 from H are delivered to a still I to recover the recyclable chlorinated materials, predominantly 1,1-dichloroethane 12 which are mixed with recyclables from product finishing system 17. The remainder of this high boiling material is removed from the process 13 and may be combined with the heavies 19 from the 1,1,1-trichloroethane product still G and these heavies either separated and/or cracked as appropriate to obtain usable higher polychlorinated hydrocarbons.

It follows that elimination of 1,2-dichloroethane from the process following its formation in the thermal chlorinator B as proposed in the description above materially reduces the severity of the purification steps to obtain the desired product, 1,1,1-trichloroethane, in a high purity.

DETAILED DESCRIPTION OF THE INVENTION

Figure 1:
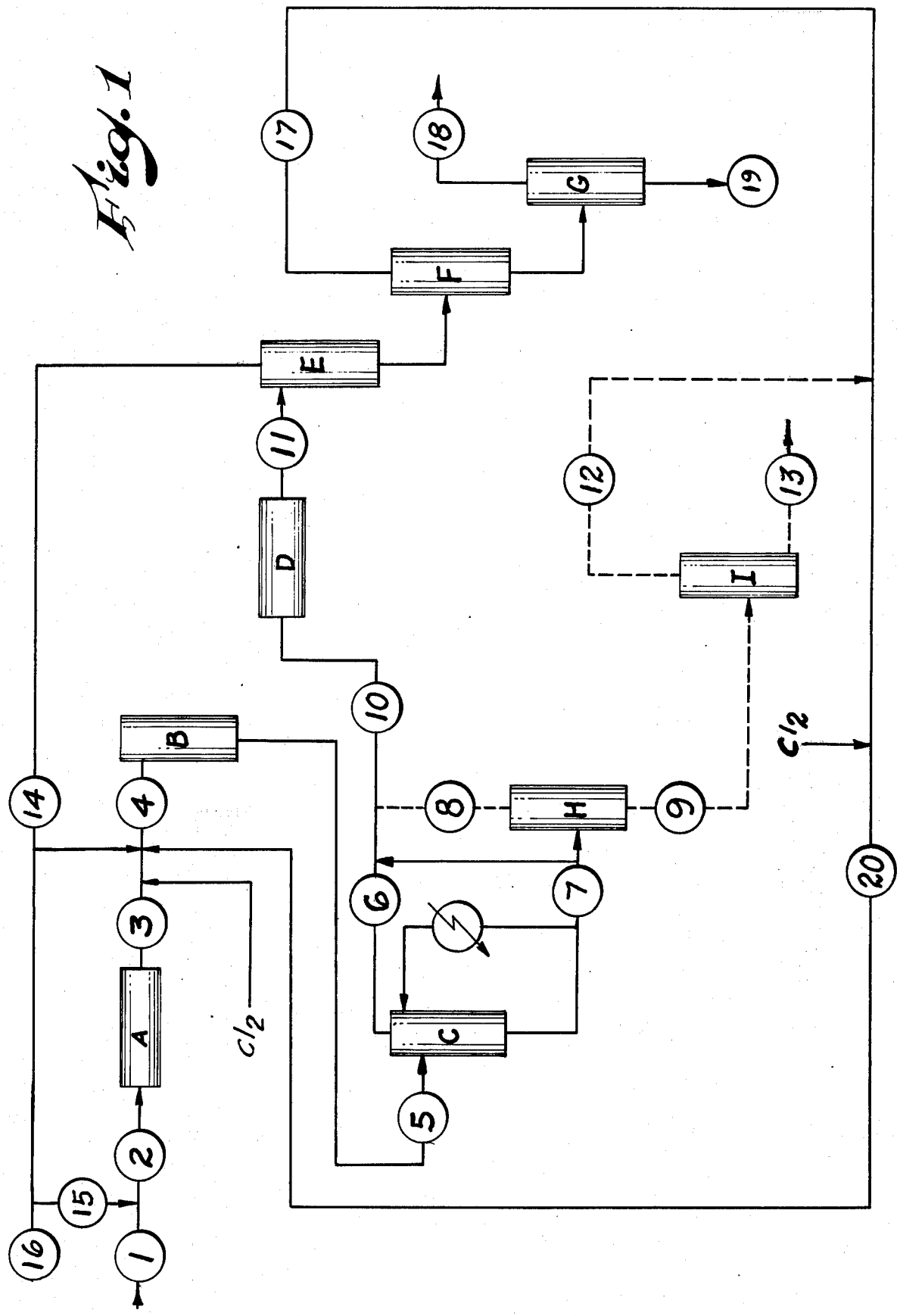

In accordance with the present invention, about 33.9 pounds ethylene (4.4 pounds of which may be separated as a product of the overall process) and about 74.6 pounds of hydrogen chloride is reacted at about 50° C and about 35 psig in the presence of aluminum chloride catalyst in a boiling bed hydrochlorinator A producing about 74.9 pounds of ethyl chloride and about 30.4 pounds excess hydrogen chloride. This is mixed together with about 21.8 pounds ethyl chloride and about 98.9 pounds 1,1-dichloroethane obtained as products of the overall reaction. This mixture is reacted in a thermal chlorination reaction zone B for about two seconds at 475° C and 40 psig with 153.7 pounds chlorine. The resulting product stream is passed into a liquid bed hydrochlorinator reactor D operating at 45° C and 35 psig where it is contacted with ferric chloride (10.4 pounds in 50.2 pounds of perchloroethylene) to produce in pounds:

| | |
|---|---|
| 134.9 | HCl (hydrogen chloride) |
| 4.39 | $C_2H_4$ (ethylene) |
| .74 | $C_2H_3Cl$ (vinyl chloride) |
| 21.77 | $C_2H_5Cl$ (ethyl chloride) |
| .95 | $1,1\text{-}C_2H_2Cl_2$ (vinylidene chloride) |
| 2.21 | $t\text{-}C_2H_2Cl_2$ (trans dichloroethylene) |
| 102.09 | $1,1\text{-}C_2H_4Cl_2$ (1,1-dichloroethane) |
| 5.27 | $c\text{-}C_2H_2Cl_2$ (cis-dichloroethylene) |
| 106.49 | $1,1,1\text{-}C_2H_3Cl_3$ (1,1,1-trichloroethane) |
| 1.57 | $C_2HCl_3$ (1,1,2-trichloroethylene) |
| 1.68 | $1,2\text{-}C_2H_4Cl_2$ (1,1-dichloroethane) |
| 4.50 | $1,1,2\text{-}C_2H_3Cl_3$ (1,1,2-trichloroethane) |
| 1.25 | $1,1,1,2\text{-}C_2H_2Cl_4$ (unsym. tetrachloroethane) |

This product stream is separated in several stills E, F and G to obtain product (1,1,1-trichloroethane), recycle streams and heavies, of which the latter are removed from the system. The hydrogen chloride, vinyl chloride, ethyl chloride, and vinylidene chloride and any unreacted ethylene are separated as overhead on a first still E and sent to the aluminum chloride hydrochlorinator A; the 1,1-$C_2H_4Cl_2$, cis-1,2-$C_2H_2Cl_2$ and trans-1,2-$C_2H_2Cl_2$ overhead from a second still F are sent to the thermal chlorination reactor B. To prevent the build-up of cis- and trans-dichloroethylenes in the reactors, they are chlorinated to tetrachloroethane enroute 20 at 25° C, care being taken to exclude light or other radiation. The 1,1,1-trichloroethane is product 18 from the third still G and the bottoms 19 from the third still are the heavies.

Further to illustrate the use of the present invention in such a multi-reaction train for producing 1,1,1-trichloroethane from ethylene and chlorine as the sole feeds as set forth in the drawing (FIG. 1), the overall feed of ethylene of about 242.8 mols/day and about 499.2 mols/day of chlorine to produce about 183.9 mols/day of 1,1,1-trichloroethane, about 39.2 mols/day of heavies (1,2-dichloroethane, trichloroethylene, 1,1,2-trichloroethane, and tetrachloroethanes). These latter compounds, the heavies, with about 381.7 mols/day of hydrogen chloride are removed from the process. Each can be employed in other processes.

To illustrate the use of a dehydrochlorination step (FIG. 1 dotted lines) a liquid such as would be obtained from the quench of a thermal chlorinator effluent (Stream 7, FIG. 1) and anhydrous ferric chloride ($FeCl_3$) are fed to a 1000 cc vessel fitted with a 30-tray distillation column. The rate of take-off from the top tray of the column is adjusted such that the overhead temperature is maintained at about 40° C. The temperature of the material remaining in the reboiler ranges between 62° and 78° C.

At the end of 7 hours, the feed pump is shut off and the system allowed to cool. During the 7 hour period, 418 grams of liquid and 0.5 grams FeCl$_3$ were fed. The table below shows the quantities of the various compounds fed and recovered:

| Component | Grams Fed | Grams Recovered |
|---|---|---|
| Vinyl chloride | 2.9 | 4.4 |
| Ethyl Chloride | 2.6 | 4.9 |
| Vinylidene Chloride | 30.2 | 203.7 |
| trans-1,2-Dichloroethylene | 6.4 | 6.7 |
| 1,1-Dichloroethane | 90.9 | 87.4 |
| 1,1,1-Trichloroethane | 227.2 | 5.8 |
| cis-1,2-Dichloroethylene | 11.1 | 8.3 |
| Trichloroethylene | 7.0 | 4.5 |
| 1,2-Dichloroethane | 9.9 | 6.1 |
| Perchloroethylene | 1.2 | 0.7 |
| 1,1,2-Trichloroethane | 20.8 | 16.4 |
| Tetrachloroethane | 8.4 | 7.6 |
| Hydrogen Chloride | — | 62.0 |
| Total | 418.6 | 418.5 |

From the above, it is obvious that 1,1,1- trichloroethane can be converted to vinylidene chloride in high yields, thus, simplifying its separation from compounds with which it is admixed in the thermal chlorinator reaction product.

The following tables set forth the streams which would be produced based on the foregoing examples to produce 25 million pounds of 1,1,1-trichloroethane in accordance with each of the alternative flow diagrams of FIG. 1. The numbers set forth in the tables are based on calculations of steady state operation for all streams. The numerical column headings correspond with the stream numbers of FIG. 1.

The process stream calculations were based on the following assumptions:

1. all distillations produce ideal separation and have no losses.
2. The aluminum chloride hydrochlorinator gives 96% yield to ethyl chloride based on both ethylene and hydrogen chloride. It also gives 100% conversion of ethylene fed. (A conservative assumption based on actual experience).
3. The thermal chlorinator gives 100% conversion of chlorine fed and has the product distribution similar to that obtained in the laboratory.
4. Quench system is operated such that all 1,1,1-trichloroethane remains in the liquid phase of the quench.
5. The ferric chloride dehydrochlorinator gives 97% conversion of 1,1,1-trichloroethane present in the thermal chlorinator product to vinylidene chloride. Other components are unaffected.
6. The ferric chloride hydrochlorinator gives:
   98% conversion of vinyl chloride to 1,1-dichloroethane
   56% conversion of ethylene to ethyl chloride
   96% conversion of vinylidene chloride to 1,1,1-trichloroethane Other components are unaffected.
7. Chlorination of 1,1-dichloroethane recycle stream gives 100% conversion of cis and trans-1,2-dichloroethylene to tetrachloroethane with 2% loss of 1,1-dichloroethane to 1,1,2-trichloroethane.
8. Compression and separation of recycle HCl and lights are ideal with no loss.

1,1,1-TRICHLOROETHANE PROCESS WITHOUT DEHYDROCHLORINATION STEP
Based on Process Producing 25 M Lbs./Year 1,1,1-Trichloroethane
Numbers are in Lb. Moles Per Year

| | 1 | 2 | 3 | 4 | 5 |
|---|---|---|---|---|---|
| Chlorine | | | | 508,561.8 | |
| Ethylene | 247,367.6 | 284,133.3 | | | 83,559.8 |
| Hydrogen Chloride | | 479,733.9 | 195,600.7 | 195,600.7 | 1,106,266.7 |
| Vinyl Chloride | | 2,778.8 | | | 138,938.6 |
| Ethyl Chloride | | 79,311.4 | 352,081.2 | 352,081.2 | 32,517.3 |
| Vinylidene Chloride | | 2,282.0 | | | 57,050.2 |
| trans-Dichloroethylene | | | | | 5,340.2 |
| 1,1-Dichloroethane | | | | 234,720.8 | 103,347.5 |
| cis-Dichloroethylene | | | | | 12,786.5 |
| 1,1,1-Trichloroethane | | | | | 103,328.0 |
| Ethylene Dichloride | | | | | 4,005.2 |
| Trichloroethylene | | | | | 2,815.0 |
| 1,1,2-Trichloroethane | | | | 4,910.7 | 13,360.9 |
| unsymm-tetrachloroethane | | | | 18,126.7 | 19,699.8 |

| | 6 | 7 | 10 | 11 | 14 |
|---|---|---|---|---|---|
| Chlorine | | | | | |
| Ethylene | 82,799.1 | 760.7 | 83,559.8 | 36,765.7 | 36,765.7 |
| Hydrogen Chloride | 1,082,753.2 | 23,513.5 | 1,106,266.7 | 868,513.6 | 868,513.6 |
| Vinyl Chloride | 122,348.8 | 16,589.8 | 138,938.6 | 2,778.8 | 2,778.8 |
| Ethyl Chloride | 29,453.9 | 3,063.4 | 32,517.3 | 79,311.4 | 79,311.4 |
| Vinylidene Chloride | 33,034.8 | 24,015.4 | 57,050.2 | 2,282.0 | 2,282.0 |
| trans-Dichloroethylene | 2,147.5 | 3,192.7 | 5,340.2 | 5,340.2 | |
| 1,1-Dichloroethane | 27,513.5 | 75,834.0 | 103,347.5 | 239,507.1 | |
| cis-Dichloroethylene | 3,430.8 | 9,355.7 | 12,786.5 | 12,786.5 | |
| 1,1,1-Trichloroethane | | 130,328.0 | 130,328.0 | 187,378.2 | |
| Ethylene Dichloride | | 4,005.2 | 4,005.2 | 4,005.2 | |
| Trichloroethylene | | 2,815.0 | 2,815.0 | 2,815.0 | |
| 1,1,2-Trichloroethane | | 13,360.9 | 13,360.9 | 13,360.9 | |
| unsymm-tetrachloroethane | | 19,699.8 | 19,699.8 | 19,699.8 | |

| | 15 | 16 | 17 | 18 | 19 | 20 |
|---|---|---|---|---|---|---|
| Chlorine | 36,765.7 | | | | | |
| Ethylene | | | | | | |
| Hydrogen Chloride | 479,733.9 | 388,810.7 | | | | |
| Vinyl Chloride | 2,778.8 | | | | | |
| Ethyl Chloride | 79,311.4 | | | | | |
| Vinylidene Chloride | 2,282.0 | | | | | |
| trans-Dichloroethylene | | | 5,340.2 | | | |
| 1,1-Dichloroethane | | | 239,507.1 | | | 234,720.8 |
| cis-Dichloroethylene | | | 12,786.5 | | | |
| 1,1,1-Trichloroethane | | | | 187,378.2 | | |
| Ethylene Dichloride | | | | | 4,005.2 | |
| Trichloroethylene | | | | | 2,815.0 | |

-continued

| | | | | | |
|---|---|---|---|---|---|
| 1,1,2-Trichloroethane | | | | 13,360.9 | 4,910.7 |
| unsymm-tetrachloroethane | | | | 19,699.8 | 18,126.7 |

1,1,1-TRICHLOROETHANE PROCESS INCLUDING DEHYDROCHLORINATION STEP

Based on Process Producing 25 M Lbs./Year 1,1,1-Trichloroethane
Numbers are in Lb. Moles Per Year

| | 1 | 2 | 3 | 4 | 5 |
|---|---|---|---|---|---|
| Chlorine | | | | 530,676 | |
| Ethylene | 258,124 | 296,489 | | | 87,193.3 |
| Hydrogen Chloride | | 500,595 | 204,106 | 204,106 | 1,154,372 |
| Vinyl Chloride | | 2,899.6 | | | 144,980 |
| Ethyl Chloride | | 82,760.2 | 367,391 | 367,391 | 33,931.3 |
| Vinylidene Chloride | | 7,656.7 | | | 59,531.0 |
| trans-Dichloroethylene | | | | | 5,572.4 |
| 1,1-Dichloroethane | | | | 244,820 | 107,842 |
| cis-Dichloroethylene | | | | | 13,342.5 |
| 1,1,1-Trichloroethane | | | | | 136,006 |
| Ethylene Dichloride | | | | | 4,179.3 |
| Trichloroethylene | | | | | 2,937.4 |
| 1,1,2-Trichloroethane | | | | 5,124.3 | 13,941.9 |
| unsymm-tetrachloroethane | | | | 18,914.9 | 20,556.4 |

| | 6 | 7 | 8 | 9 | 10 |
|---|---|---|---|---|---|
| Chlorine | | | | | |
| Ethylene | 86,399.6 | 793.75 | 793.75 | | 87,193.3 |
| Hydrogen Chloride | 1,129,836 | 24,536.0 | 156,460 | | 1,286,296 |
| Vinyl Chloride | 127,669 | 17,311.2 | 17,311.2 | | 144,980 |
| Ethyl Chloride | 30.734.7 | 3,196.6 | 3,196.6 | | 33,931.3 |
| Vinylidene Chloride | 34,471.3 | 25,059.7 | 156,984 | | 191,455 |
| trans-Dichloroethylene | 2,240.9 | 3,331.6 | | 3,331.6 | 2,240.9 |
| 1,1-Dichloroethane | 28,709.9 | 79,131.7 | | 79,131.7 | 28,709.9 |
| cis-Dichloroethylene | 3,580.0 | 9,762.5 | | 9,762.5 | 3,580.0 |
| 1,1,1-Trichloroethane | | 136,006 | | 4,082.1 | |
| Ethylene Dichloride | | 4,179.3 | | 4,179.3 | |
| Trichloroethylene | | 2,937.4 | | 2,937.4 | |
| 1,1,2-Trichloroethane | | 13,941.9 | | 13,941.9 | |
| unsymm-tetrachloroethane | | 20,556.4 | | 20,556.4 | |

| | 11 | 12 | 13 | 14 | 15 |
|---|---|---|---|---|---|
| Chlorine | | | | | |
| Ethylene | 38,364.4 | | | 38,364.4 | 38,364.4 |
| Hydrogen Chloride | 911,588 | | | 911,588 | 500,595 |
| Vinyl Chloride | 2,899.6 | | | 2,899.6 | 2,899.6 |
| Ethyl Chloride | 82,760.2 | | | 82,760.2 | 82,760.2 |
| Vinylidene Chloride | 7,656.7 | | | 7,656.7 | 7,656.7 |
| trans-Dichloroethylene | 2,240.9 | 3,331.6 | | | |
| 1,1-Dichloroethane | 170,791 | 79,131.7 | | | |
| cis-Dichloroethylene | 3,580.0 | 9,762.5 | | | |
| 1,1,1-Trichloroethane | 187,378 | | 4,082.1 | | |
| Ethylene Dichloride | | | 4,179.3 | | |
| Trichloroethylene | | | 2,937.4 | | |
| 1,1,2-Trichloroethane | | | 13,941.9 | | |
| unsymm-tetrachloroethane | | | 20,556.4 | | |

| | 16 | 17 | 18 | 20 |
|---|---|---|---|---|
| Chlorine | | | | |
| Ethylene | | | | |
| Hydrogen Chloride | 410,993 | | | |
| Vinyl Chloride | | | | |
| Ethyl Chloride | | | | |
| Vinylidene Chloride | | | | |
| trans-Dichloroethylene | | 2,240.9 | | |
| 1,1-Dichloroethane | | 170,791 | | 244,820 |
| cis-Dichloroethylene | | 3,580.0 | | |
| 1,1,1-Trichloroethane | | | 187,378 | |
| Ethylene Dichloride | | | | |
| Trichloroethylene | | | | |
| 1,1,2-Trichloroethane | | | 5,124.3 | |
| unsymm-tetrachloroethane | | | 18,914.9 | |

What is claimed is:

1. A method for preparing 1,1,1-trichloroethane which comprises:
   1. reacting ethylene, recycle ethylene from a later step in the process and hydrogen chloride, said hydrogen chloride being obtained from another step in the process, together in a liquid boiling reaction medium in the presence of a Fridel-Crafts aluminum chloride (AlCl$_3$) catalyst thereby to produce predominantly ethyl chloride;
   2. reacting in the gas phase in a thermal reactor the so-produced ethyl chloride, recycle ethyl chloride from a later step and recycle 1,1-dichloroethane stream from another step in the process with chlorine at a temperature of from 400° to b 550° C;
   3. subjecting the so-produced reaction mixture from the thermal chlorination Step (2) to a hydrochlorination reaction in a liquid reaction medium in the presence of a Friedel-Crafts ferric chloride (FeCl$_3$) catalyst to convert vinylidene chloride in the said so-produced thermal chlorination reaction mixture to 1,1,1-trichloroethane and vinyl chloride in said so-produced thermal chlorination reaction mixture to 1,1-dichloroethane;
   4. separating the hydrochlorination reaction mixture from Step (3) by distillation to recover a) 1,1,1-trichloroethane, as product, b) a lights fraction predominantly comprised of ethylene, ethyl chloride, and hydrogen chloride for recycling to Step (1), and c) a recycle fraction boiling between about 37° and about 60° C at atmospheric pressure which is principally 1,1-dichloroethane for recycle to Step (2).

2. A method for preparing 1,1,1-trichloroethane which comprises:
   1. reacting ethylene, recycle ethylene from a later step in the process and hydrogen chloride, said hydrogen chloride being obtained from another step in the process, together in a boiling liquid reaction medium in the presence of a Friedel-Crafts aluminum chloride (AlCl$_3$) catalyst thereby to produce predominantly ethyl chloride;
   2. reacting in the gas phase in a thermal reactor the so-produced ethyl chloride, recycle ethyl chloride from a latter step and a predominantly 1,1-dichloroethane stream from another step in the process with chlorine at a temperature of from 400° to 550° C;
   3. subjecting the so-produced reaction mixture from the thermal chlorination Step (2) to a quench step, separating the quenched thermal chlorination reaction mixture into a fraction boiling below about 40° C and a fraction boiling above about 40° C;
   4. subjecting the fraction from step (3) boiling above about 40° C to dehydrochlorination in a boiling liquid reaction medium in the presence of a Friedel-Crafts ferric chloride (FeCl$_3$) catalyst to convert the 1,1,1-trichloroethane therein to vinylidene chloride;
   5. separating the dehydrochlorination reaction mixture from Step (4) into a fraction boiling below about 60° C predominantly comprised of vinylidenechloride and into a fraction boiling above about 60° C;
   6. combining the fraction boiling below about 60° C from Step 5 with the fraction boiling below about 40° C from Step 3 and subjecting the resultant mixture to hydrochlorination in a liquid reaction medium in the presence of a Friedel-Crafts ferric chloride (FeCl$_3$) catalyst to convert vinylidene chloride therein to 1,1,1-trichloroethane and vinyl chloride therein to 1,1-dichloroethane;
   7. separating the hydrochlorination reaction mixture from Step (6) by distillation to recover a) 1,1,1-trichloroethane, as product, b) a lights fraction predominantly comprised of ethylene, ethyl chloride and hydrogen chloride for recycling to Step (1), and c) a recycle fraction boiling between about 37° and about 60° C at atmospheric pressure which is principally 1,1-dichloroethane for recycle to Step (2).
   8. subjecting the fraction boiling above about 60° C from Step (5) to a distillation to recover recyclable chlorinated materials comprised predominantly of 1,1-dichloroethane for recycle to Step (2).

3. A method for preparing 1,1,1-trichloroethane which comprises:
   1. reacting ethylene, recycle ethylene from a later step in the process and hydrogen chloride, said hydrogen chloride being obtained from another step in the process, together in a boiling liquid reaction medium in the presence of a Friedel-Crafts aluminum chloride (AlCl$_3$) catalyst thereby to produce predominantly ethyl chloride;
   2. reacting in the gas phase in a thermal reactor the so-produced ethyl chloride, recycle ethyl chloride from a later step and a predominantly 1,1-dichloroethane stream from a later step in the process with chlorine at a temperature of from 400° to 550° C;
   3. subjecting the so-produced reaction mixture from the thermal chlorination Step (2) to hydrochlorination in a liquid reaction medium in the presence of a Friedel-Crafts ferric chloride (FeCl$_3$) catalyst to convert vinylidene chloride in the said so-produced thermal chlorination reaction mixture to 1,1,1-trichloroethane and vinyl chloride in said so-produced thermal chlorination reaction mixture to 1,1-dichloroethane;
   4. separating the hydrochlorination reaction mixture from Step (3) by distillation to recover a). 1,1,1-trichloroethane, as product, b). a lights fraction predominantly comprised of ethylene, ethyl chloride and hydrogen chloride for recycling to Step (1), c). a fraction boiling between about 37° and about 60° C at atmospheric pressure which is principally 1,1-dichloroethane and cis and trans 1,2-dichloroethylenes; and d). a fraction consisting essentially of higher boiling polychlorinated ethanes including tetrachloroethanes;
   5. chlorinating the 1,1-dichloroethane containing fraction from Step (4) c) in the dark in the absence of catalyst to chlorinate the cis- and trans-1,2-dichloroethylene to tetrachloroethane;
   b. recycling the so-produced chlorination reaction mixture from Step (5) to Step (2).

4. A method for preparing 1,1,1-trichloroethane which comprises:
   1. reacting ethylene, recycle ethylene from a later step in the process and hydrogen chloride, said hydrogen chloride being obtained from another step in the process, together in a boiling liquid reaction medium in the presence of a Friedel-Crafts aluminum chloride (AlCl$_3$) catalyst thereby to produce predominantly ethyl chloride;
   2. reacting in the gas phase in a thermal reactor the so-produced ethyl chloride, recycle ethyl chloride from a later step and a predominantly 1,1-dichloroethane stream from another step in the process with chlorine at a temperature of from 400° to to 550° C;
   3. subjecting the so-produced reaction mixture from the thermal chlorination Step (2) to a quench step, separating the quenched thermal chlorination reaction mixture into a) a fraction boiling below about 40° C and b) a fraction boiling above about 40° C;
   4. subjecting the fraction from Step (3) boiling above about 40° C to dehydrochlorination in a boiling reaction medium in the presence of a Friedel-Crafts ferric chloride (FeCl$_3$) catalyst to convert the 1,1,1-trichloroethane therein to vinylidene chloride;
   5. separating the dehydrochlorination reaction mixture from Step (4) into a fraction boiling below about 60° C predominantly comprised of vinylidene chloride and into a fraction boiling above about 60° C;
   6. combining the fraction boiling below about 60° C from Step (5) with the fraction boiling below about 40° C from Step 4 and subjecting the resultant mixture to hydrochlorination in a liquid reaction medium in the presence of a Friedel-Crafts ferric chloride (FeCl$_3$) catalyst to convert vinylidene chloride therein to 1,1,1-trichloroethane and vinyl chloride therein to 1,1-dichloroethane;
   7. separating the hydrochlorination reaction mixture from Step (6) by distillation to recover a) 1,1,1-trichloroethane, as product, b) a lights fraction predominantly comprised of ethylene, ethyl chloride and hydrogen chloride for recycling to Step (1), and c) a fraction boiling between about 37° and about 60° C at atmospheric pressure which is principally 1,1-dichloroethane and cis- and trans-1,2-dichloroethylene;

8. subjecting the fraction boiling above about 60° C from Step (5) to a distillation to recover recyclable chlorinated materials comprised predominantly of 1,1-dichloroethane and cis- and trans-1,2-dichloroethylene;

9. combining the fraction obtained from Step (7) (c) and the recyclable chlorinated materials obtained by distillation in Step (8) and subjecting the resultant mixture comprised predominantly of 1,1-dichloroethane and cis- and trans-1,2-dichloroethylene to a distillation to remove the trans-1,2-dichloroethylene from said resultant mixture and recovering a fraction comprised predominantly of 1,1-dichloroethane and cis-1,2-dichloroethylene;

10. recycling the fraction comprised predominantly of 1,1-dichloroethane and cis-1,2-dichloroethylene from Step (9) to the thermal gas phase chlorination Step (2) wherein said cis-1,2-dichloroethylene will isomerize to an equilibrium mixture of cis-trans forms of 1,2-dichloroethylenes which will eventually be subjected to distillation Step (9) to remove the trans form so formed and thereby to prevent build-up of the 1,2-dichloroethylenes in the recycle.

* * * * *

UNITED STATES PATENT AND TRADEMARK OFFICE
CERTIFICATE OF CORRECTION

PATENT NO. : 4,048,241

DATED : September 13, 1977

INVENTOR(S) : Theodore S. Boozalis; Darryl E. Cragar; John B. Ivy; Gordon G. Willis It is certified that error appears in the above-identified patent and that said Letters Patent are hereby corrected as shown below:

Col. 1 of title page, in [22] delete "1965" and insert -- 1975 --

Col. 2, of title page, in [56] delete "260/653" and insert -- 260/663 --

Col. 2, line 29, delete "and" and insert -- are --

Col. 6, number 6., insert a period "." after "1,1,1-trichloroethane" and start a new paragraph with "Other components are unaffected."

Col. 7 in the second section under col. 6, delete "30.734.7" and insert -- 30,734.7 --

Col. 7, line 68, delete "b" before "550°C;"

Col. 9, line 15, delete "latter" and insert -- later --

Col. 9, line 33, delete "vinylidenechloride" and insert -- vinylidene chloride --

Col. 10, line 27, delete "b." and insert -- 6. --

UNITED STATES PATENT OFFICE
CERTIFICATE OF CORRECTION

Patent No. 4,048,241      Dated September 13, 1977

Inventor(s)    Theodore S. Boozalis et al.

It is certified that error appears in the above-identified patent and that said Letters Patent are hereby corrected as shown below:

Column 10, line 43, delete the extra "to" before "550°C;"

Signed and Sealed this

Twenty-first Day of February 1978

[SEAL]

Attest:

RUTH C. MASON  
*Attesting Officer*

LUTRELLE F. PARKER  
*Acting Commissioner of Patents and Trademarks*